United States Patent [19]

Bakshi

[11] 4,364,748

[45] Dec. 21, 1982

[54] PROCESS FOR RECOVERING MALEIC ANHYDRIDE BY CONDENSATION

[75] Inventor: Kiran R. Bakshi, El Cerrito, Calif.

[73] Assignee: Chevron Research Company, San Francisco, Calif.

[21] Appl. No.: 11,972

[22] Filed: Feb. 14, 1979

Related U.S. Application Data

[63] Continuation of Ser. No. 809,734, Jun. 24, 1977, abandoned.

[51] Int. Cl.³ .............................................. B01D 19/00
[52] U.S. Cl. ......................................... 55/27; 55/48; 55/55; 549/262
[58] Field of Search ................... 55/27, 48, 55, 80, 82; 260/346.76

[56] References Cited

U.S. PATENT DOCUMENTS

| | | | |
|---|---|---|---|
| 2,211,160 | 8/1940 | Punnett | 260/346.76 |
| 2,670,355 | 2/1954 | Barsky et al. | 260/346.76 |
| 2,812,037 | 11/1957 | Stephan et al. | 55/82 |
| 3,476,775 | 11/1969 | Sueur | 260/346.76 |
| 3,642,829 | 2/1972 | Weyens | 260/346.76 |
| 3,818,680 | 6/1974 | Marquis | 55/48 |

FOREIGN PATENT DOCUMENTS 789414  1/1958  United Kingdom .......... 260/346.76

*Primary Examiner*—Robert H. Spitzer
*Attorney, Agent, or Firm*—D. A. Newell; T. G. De Jonghe; C. J. Caroli

[57] ABSTRACT

A process for recovering maleic anhydride from gaseous compositions comprising maleic anhydride and water by condensing the composition at a temperature in the range of from about 20° C. to about 50° C. and a pressure of less than about 200 millimeters of mercury.

5 Claims, No Drawings

PROCESS FOR RECOVERING MALEIC ANHYDRIDE BY CONDENSATION

CROSS-REFERENCE TO RELATED APPLICATION

This application is a continuation of U.S. application Ser. No. 809,734, filed June 24, 1977, now abandoned.

BACKGROUND OF THE INVENTION

This invention concerns a process for recovering maleic anhydride from gaseous compositions which comprise water as well as maleic anhydride. The process is carried out by condensing the gas under select temperature and pressure conditions. In this way, maleic anhydride is collected as a condensate while light impurities such as water and acids remain in the vapor phase.

This process is particularly adaptable to the recovery of maleic anhydride which is normally lost during the light stripping of crude maleic anhydride. Crude maleic anhydride is produced by the vapor phase oxidation of a hydrocarbon feed, and is recovered by absorption from the oxidation effluent using a liquid solvent followed by distillation of the anhydride-rich absorbent. U.S. Pat. No. 3,818,680 to Marquis thoroughly describes a typical process for producing crude maleic anhydride using a liquid intramolecular carboxylic acid absorbent. Other organic absorbents can be used such as those disclosed in U.S. Pat. Nos. 2,574,644; 3,040,059; 2,893,924; 3,891,680; and 3,850,758.

It is conventional practice to further refine the crude maleic anhydride by stripping off low-boiling impurities using reduced pressure distillation. In general, the low-boiling impurities comprise carboxylic acids such as acetic and acrylic acids and water. However, under even the best of operating conditions, the overhead vapor will also contain some maleic anhydride which is either lost through the vacuum system or recovered through an elaborate absorption and recycle process. Thus, the overhead vapor comprises maleic anhydride and water. Conventional absorption processing has been tried as a method of recovering the anhydride, but has several drawbacks. In particular, a significant proportion of the impurities must also be absorbed and recycled to insure complete anhydride recovery. Thus, using absorption to recover the anhydride from the light stripper overhead vapor is a relatively inefficient process.

Accordingly, it would be advantageous to provide a process for recovering maleic anhydride from gaseous mixtures also containing water and low-boiling impurities which while recovering the anhydride leaves the water and other impurities in the gas.

Several U.S. patents discuss the recovery of maleic anhydride from gaseous compositions also containing water. In general, these methods use partial condensation of maleic anhydride effected by cooling the gaseous composition to temperatures above 50° C. so as to minimize condensation of water. Such practice, however, results in only partial recovery of maleic anhydride contaminated with some maleic acid, since any attempt at complete recovery requires cooling the gas below the water dew point. If the water dew point is reached, the maleic anhydride will hydrolyze to maleic and fumaric acids. Thus, for example, British Pat. No. 822,612 teaches diluting the effluent gas from the oxidation reactor with an inert gas until the anhydride partial pressure is less than 2.24 millimeters of mercury and cooling the gas to about 20° C. Similarly, U.S. Pat. No. 2,762,449; U.S. Pat. No. 2,812,037; and French Pat. No. 1,303,126 teach partial condensation processes for recovering maleic anhydride by cooling the gas to temperatures between 50°–60° C. from gas compositions comprising the anhydride and relatively low concentrations of water. In summary, prior art teaches recovery of maleic anhydride by cooling maleic anhydride gases at about one atmosphere pressure.

The prior art partial condensations are particularly useful where the concentration of anhydride is relatively high and concentration of water relatively low, usually less than 5 volume %, such that the over-all efficiency of the recovery is not significantly reduced by leaving minor amounts of anhydride in the gas. However, it is still desirable to provide a process which provides essentially complete recovery of anhydride even where the concentration of water is relatively high, typically more than 10 volume %.

SUMMARY OF THE INVENTION

It has now been found that maleic anhydride in a gaseous composition with water can be recovered, without significant water contamination, by condensing the composition at a temperature between about 20° C. and 50° C., preferably between about 25° C. and 40° C. and a pressure of less than about 200 mm, preferably from about 25 mm to about 100 mm or from about 25 mm to about 50 mm.

DETAILED DESCRIPTION OF THE INVENTION

According to this invention, maleic anhydride can be recovered from gaseous mixtures with water without appreciable loss of the anhydride, and without appreciable loss of efficiency by condensing the gas containing water and maleic anhydride at reduced pressure. Generally, gas streams containing both water and maleic anhydride cannot be condensed because of the possibility that enough water will condense with the anhydride to cause hydrolysis of the anhydride to maleic acid. Maleic acid readily isomerizes to solid fumaric acid which is insoluble. However, it has been found that under the select conditions of this invention, such gaseous mixtures can be condensed to recover maleic anhydride without consequent water condensation. Condensation of the mixtures can be carried out at a temperature between about 20° C. and 50° C. at a reduced pressure of less than about 200 mm.

In a preferred embodiment, the process is used to recover residual maleic anhydride contained in the gaseous overheads from the distillation of crude maleic anhydride. Such compositions generally comprise from about 1 to about 30 percent by volume maleic anhydride and from about 10 to about 70 percent by volume water. In accordance with this invention, the overhead vapor containing residual maleic anhydride and low-boiling impurities is passed to a condenser system. The condenser system is maintained at a temperature of from about 20° C. to 50° C. at a pressure of less than 200 millimeters of mercury. The condensate from the condenser system, containing liquid maleic anhydride, can be recycled and the vaporous impurities can be vented through the vacuum system.

The following example further illustrates the process of this invention applied to the recovery of maleic anhydride from the light stripper overhead vapors of a crude maleic anhydride distillation process, and suggests additional embodiments within the scope of the following claims.

EXAMPLE

A crude maleic anhydride product stream was obtained by oxidizing n-butane according to the process described in U.S. Pat. No. 3,864,280, which issued Feb. 4, 1975 to Schneider. The concentrations of components in the product stream are shown in Table I. For such a composition, the dew points of water and maleic anhydride at various total pressures are given in Table II. The stream was condensed by passing it through a condenser cooled by a countercurrent flow of air through the jacket. In a typical run, for example, 2 gmols/hr of this stream was passed through a condenser with a heat transfer area of 0.3 sq. ft.

As condensation proceeded, crystals of maleic anhydride were formed on the heat exchanger walls. The exhaust from the condenser was scrubbed and analyzed for its composition by potentiometric titration for organic acids and by gas chromatography for complete composition.

The condensed maleic anhydride was then analyzed for trace impurities such as maleic acid, fumaric acid, light organic acids and other organic impurities by various methods such as freezing point, preferential solubility in chloroform, infra-red spectrometry and gas chromatography.

Table III lists the run conditions and the results of these analyses. Efficiency of maleic anhydride recovery by this condensation process was obtained from analyses of the condensed maleic anhydride and the exhaust gas composition leaving the condenser in operation. Data in Table III shows that maintaining a temperature of more than about 20° C., preferably more than about 30° C., and a pressure of less than about 50 mm Hg results in undetectably small amount of water condensation or hydration of condensed maleic anhydride to maleic acid of fumaric acid. Other organic impurities were also rejected under these conditions to provide high quality of maleic anhydride shown by increased color stability.

TABLE I

| Typical Composition of Crude Maleic Anhydride Distillation Overhead | |
|---|---|
| Component | Volume % |
| n-butane | 0.69 |
| water | 49.39 |
| oxygen | 5.13 |
| nitrogen | 21.87 |
| carbon oxides | 1.84 |
| acetic acid | 6.68 |
| acrylic acid | 5.56 |
| butyric acid | 0.18 |
| maleic anhydride | 8.66 |
| Total | 100.00 |

TABLE II

| Dew Points For Water and Maleic Anhydride In Stream With Composition Of Table I | | |
|---|---|---|
| Condenser Pressure mm Hg | Dew Point Temperature, °F. | |
| | Water | Maleic Anhydride |
| 20 | 52 | 118 |
| 25 | 58 | 126 |
| 30 | 63 | 129 |
| 50 | 78 | 145 |
| 70 | 89 | 156 |

TABLE III

| Run No. | Condenser Temp. (°C.) | Condenser Pressure (mm Hg) | MA Condenser Efficiency % | Wt. % Organic Acids in Condensed MA | ppm Maleic & Fumaric Acids in Condensed MA |
|---|---|---|---|---|---|
| 1 | 37.8 | 20 | 86 | 0.3 | <300 |
| 2 | 37.8 | 25 | 82 | 0.42 | <300 |
| 3 | 37.8 | 30 | 79 | 0.49 | <300 |
| 4 | 37.8 | 50 | 78 | 0.8 | <300 |
| 5 | 32.2 | 30 | 82 | 0.7 | <300 |
| 6 | 23.9 | 30 | 85 | 1.88 | 1000-2000 |
| 7 | 21.1 | 30 | 94 | 2.7 | 2500-5000 |

What is claimed is:

1. A process for recovering maleic anhydride from gaseous compositions containing maleic anhydride and water, comprising cooling said composition to a temperature in the range of from about 25° C. to about 40° C. at a pressure less than about 50 millimeters of mercury thereby to obtain solid maleic anhydride having less than 300 ppm of maleic acid and fumaric acid impurities.

2. A process according to claim 1 wherein the gaseous composition comprises from about 1 to about 30 percent by volume maleic anhydride and from about 10 to about 70 percent by volume water.

3. A process according to claim 1 wherein the composition is cooled to a temperature of about 30° C.

4. In a process for stripping low-boiling impurities from crude maleic anhydride produced by the vapor phase oxidation of a hydrocarbon feedstock; the improvement which comprises, passing the lights stripper overhead vapor containing, by volume, about 1 to 30 percent maleic anhydride and about 10 to 70 percent water, through a condenser system maintained at a temperature in the range of from about 25° C. to 40° C. at less than about 50 millimeters of mercury pressure thereby to obtain solid maleic anhydride having less than 300 ppm of maleic acid and fumaric acid impurities.

5. A process according to claim 4 wherein maleic anhydride recovered in the condenser system is recycled to the lights stripper.

* * * * *